US009179988B2

(12) United States Patent
Dumitrescu et al.

(10) Patent No.: US 9,179,988 B2
(45) Date of Patent: Nov. 10, 2015

(54) DENTAL PROSTHESIS CONNECTOR DESIGN

(75) Inventors: Ion Dumitrescu, Quebec (CA); David Giasson, Quebec (CA)

(73) Assignee: Biocad Medical, Inc., Quebec (CA)

( * ) Notice: Subject to any disclaimer, the term of this patent is extended or adjusted under 35 U.S.C. 154(b) by 919 days.

(21) Appl. No.: 12/787,116

(22) Filed: May 25, 2010

(65) Prior Publication Data

US 2011/0295402 A1   Dec. 1, 2011

(51) Int. Cl.
| | |
|---|---|
| G06F 17/50 | (2006.01) |
| G06F 17/00 | (2006.01) |
| G06F 19/00 | (2011.01) |
| A61C 3/00 | (2006.01) |
| A61C 13/00 | (2006.01) |

(52) U.S. Cl.
CPC .................................. *A61C 13/0004* (2013.01)

(58) Field of Classification Search
CPC ............................ G06F 17/50; A61C 13/0004
USPC ......... 703/1; 700/98, 103, 106, 118; 433/167, 433/24
See application file for complete search history.

(56) References Cited

U.S. PATENT DOCUMENTS

| | | | |
|---|---|---|---|
| 5,027,281 A | 6/1991 | Rekow et al. | |
| 6,049,743 A | 4/2000 | Baba | |
| 6,328,567 B1 | 12/2001 | Morris et al. | |
| 6,648,640 B2 | 11/2003 | Rubbert et al. | |
| 7,013,191 B2 * | 3/2006 | Rubbert et al. | 700/98 |
| 7,029,275 B2 * | 4/2006 | Rubbert et al. | 433/24 |
| 7,156,655 B2 | 1/2007 | Sachdeva et al. | |
| 7,245,753 B2 | 7/2007 | Squilla et al. | |
| 7,322,824 B2 | 1/2008 | Schmitt | |

(Continued)

FOREIGN PATENT DOCUMENTS

| | | |
|---|---|---|
| WO | WO 2004/084756 | 10/2004 |
| WO | WO 2004/098443 | 11/2004 |

OTHER PUBLICATIONS

Andriani Daskalaki, Dental Computing and Applications: Advanced Techniques for Clinical Dentistry, Apr. 30, 2009, IGI Global, pp. 1-384.*

(Continued)

*Primary Examiner* — Kamini S Shah
*Assistant Examiner* — Juan Ochoa
(74) *Attorney, Agent, or Firm* — Knobbe Martens Olson & Bear LLP

(57) ABSTRACT

Presented herein are methods, systems, devices, and computer-readable media for dental prosthesis connector design. Embodiments include providing a computer-based interface for manipulating a connector that connects a first dental restoration component and a second dental restoration component in a dental prosthesis; providing, via a cross-sectional representation of the connector, an acceptability design constraint for the connector, such as whether the connector meets production constraints and/or encompasses the intersection between neighboring teeth; modifying the connector based on operator input; determining whether the modified connector is acceptable with respect to the acceptability design constraint; and providing an acceptability indication for the modified connector, wherein said the acceptability indication is determined based at least in part on whether the modified connector is acceptable with respect to the acceptability design constraint.

19 Claims, 9 Drawing Sheets

(56) References Cited

U.S. PATENT DOCUMENTS

| | | |
|---|---|---|
| 7,590,462 B2* | 9/2009 | Rubbert et al. ............... 700/98 |
| 7,717,708 B2 | 5/2010 | Sachdeva et al. |
| 7,856,286 B2* | 12/2010 | Kraemer et al. ............... 700/98 |
| 8,021,147 B2 | 9/2011 | Sporbert et al. |
| 8,121,718 B2* | 2/2012 | Rubbert et al. ............... 700/98 |
| 8,177,551 B2 | 5/2012 | Sachdeva et al. |
| 8,359,114 B2* | 1/2013 | Steingart et al. ............... 700/98 |
| 8,425,229 B2 | 4/2013 | Nilsson et al. |
| 8,457,772 B2 | 6/2013 | Giasson et al. |
| 2002/0028417 A1 | 3/2002 | Chapoulaud et al. |
| 2003/0039389 A1 | 2/2003 | Jones et al. |
| 2004/0081938 A1 | 4/2004 | Chishti et al. |
| 2004/0197727 A1 | 10/2004 | Sachdeva et al. |
| 2004/0220691 A1 | 11/2004 | Hofmeister et al. |
| 2004/0265770 A1 | 12/2004 | Chapoulaud et al. |
| 2005/0089822 A1* | 4/2005 | Geng ............... 433/215 |
| 2005/0186540 A1 | 8/2005 | Taub et al. |
| 2006/0020363 A1 | 1/2006 | Orth et al. |
| 2006/0063135 A1 | 3/2006 | Mehl |
| 2006/0115793 A1 | 6/2006 | Kopelman et al. |
| 2006/0122719 A1 | 6/2006 | Kopelman et al. |
| 2006/0183082 A1 | 8/2006 | Quadling et al. |
| 2006/0204078 A1 | 9/2006 | Orth et al. |
| 2006/0246402 A1 | 11/2006 | Kraemer et al. |
| 2006/0275736 A1 | 12/2006 | Wen et al. |
| 2006/0275737 A1 | 12/2006 | Kopelman et al. |
| 2007/0207437 A1 | 9/2007 | Sachdeva et al. |
| 2007/0233299 A1 | 10/2007 | Kopelman et al. |
| 2007/0292821 A1 | 12/2007 | De Vreese |
| 2008/0077270 A1* | 3/2008 | Maier et al. ............... 700/163 |
| 2008/0096151 A1 | 4/2008 | Cinader et al. |
| 2008/0220395 A1* | 9/2008 | Marshall et al. ............... 433/215 |
| 2008/0261165 A1* | 10/2008 | Steingart et al. ............... 433/24 |
| 2009/0053677 A1 | 2/2009 | Orth |
| 2009/0133260 A1 | 5/2009 | Durbin et al. |
| 2009/0248184 A1 | 10/2009 | Steingart et al. |
| 2009/0325128 A1 | 12/2009 | Holzner et al. |
| 2010/0119996 A1 | 5/2010 | Kaigler |
| 2010/0151417 A1 | 6/2010 | Nilsson et al. |
| 2011/0196524 A1 | 8/2011 | Giasson et al. |
| 2011/0196653 A1 | 8/2011 | Lajoie et al. |
| 2011/0196654 A1 | 8/2011 | Genest et al. |
| 2011/0224955 A1 | 9/2011 | Fisker et al. |
| 2011/0295402 A1 | 12/2011 | Dumitrescu et al. |
| 2012/0015316 A1 | 1/2012 | Sachdeva et al. |
| 2012/0015328 A1 | 1/2012 | Giasson et al. |
| 2012/0065985 A1 | 3/2012 | Royal et al. |
| 2012/0070803 A1 | 3/2012 | Manai et al. |
| 2012/0072177 A1 | 3/2012 | Manai et al. |
| 2012/0072178 A1 | 3/2012 | Beaudry et al. |

OTHER PUBLICATIONS

Andriani Daskalaki, Dental Computing and Applications: Advanced Techniques for Clinical Dentistry, Apr. 30 2009, IGI Global, pp. 1-384.*

Aug. 31, 2011 International Search Report and Written Opinion for International Application No. PCT/EP2011/002570 Filed May 24, 2011.

* cited by examiner

DENTAL PROSTHESIS CONNECTOR DESIGN

BACKGROUND

1. Field

The present application generally relates to planning of dental prostheses, and more particularly to dental prosthesis connector design.

2. Description of Related Technology

The use of computer systems to design dental prostheses has increased in recent years. The computer systems allow a dentist, dental technician, or other operator to design dental prostheses for individual patients. These individual prosthetic designs are often called "situations," "dental plans," or "prosthetic plans." Operators using the computer systems can design plans based on a library of the teeth shapes and positions, patient data, and/or available equipment and hardware. For example, an operator may design a dental plan that has multiple dental restoration components. Further, the operator may design an anatomical or aesthetic prosthesis, such as a full anatomic crown. Multi-tooth prostheses may require connectors between the dental restoration components. There may be, however, acceptability design constraints on the connectors due to the material used for the prosthesis, due to the production technique being used, due to the span or distance between, e.g., a crown and a pontic or two pontics in a bridge, and/or other acceptability design constraints.

A problem with current systems is that they do not adequately assist operators in designing connectors for dental plans that are within the connectors' constraints.

These problems and others are addressed by the systems, methods, and devices and computer-readable media described herein.

SUMMARY

Presented herein are methods, systems, devices, and computer-readable media for dental prosthesis connector design. This summary in no way limits the invention herein, but instead is provided to summarize a few of the embodiments.

Embodiments herein include systems, techniques, computer-readable media, and methods for dental prosthesis connector design. For example, in some embodiments, a computer system may be programmed to provide a computer-based interface for manipulating a connector, wherein the connector connects a first dental restoration component and a second dental restoration component, and wherein the connector, the first dental restoration component, and second dental restoration component are part of a prosthesis; represent, via a cross-sectional representation of the connector on the computer-based interface, an acceptability design constraint for the connector; accept operator input to modify the connector; determine whether the modified connector is acceptable with respect to the acceptability design constraint; and provide an acceptability indication for the modified connector, wherein said acceptability indication is determined based at least in part on whether the modified connector is acceptable with respect to the acceptability design constraint.

In various embodiments, the acceptability indication is an indication that a connection curve between the connector and the first dental restoration component overlaps an unacceptable production area. Determining whether the modified connector is acceptable may include, in some embodiments, determining whether the modified connector is acceptable relative to an intersection of the first dental restoration component and the second dental restoration component.

Numerous other embodiments are described throughout herein.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes for one advantage or group of advantages as taught or suggested herein without necessarily achieving other objects or advantages taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

DETAILED DESCRIPTION

Overview

Figure 1:
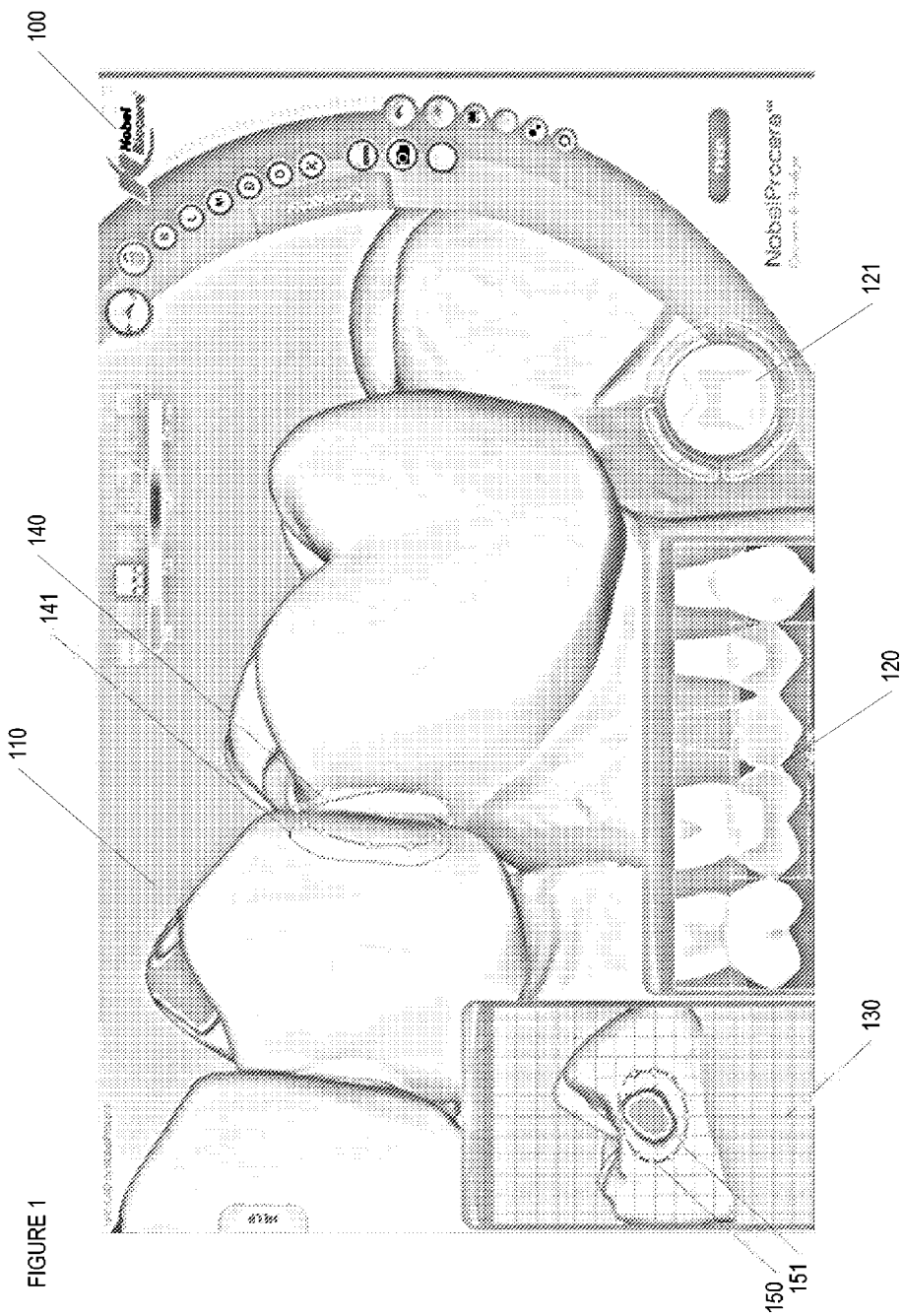
FIG. 1 illustrates a first display for dental prosthesis connector design.

Three-dimensional ("3D") or computer-aided design ("CAD") software can be used for dental prosthesis design. An operator can plan the dental prosthesis by building up and manipulating various aspects of the dental plan in the 3D or CAD software. The input data for such systems may include models made based on 3D scans of patient-specific anatomy, prostheses, and/or hardware. The 3D scans of patient-specific anatomy, prostheses, and/or hardware may be obtained via a system for scanning patient data, such as that described in U.S. patent application Ser. No. 12/703,596, entitled "DENTAL DATA PLANNING," filed Feb. 10, 2010, which is hereby incorporated by reference in its entirety for all purposes.

The input data and models may also include standard or default prostheses, hardware, or libraries of teeth, any of which can be manually or automatically adapted to the patient's anatomy. The operator may plan a full anatomic prosthesis, such as a full anatomic bridge, crown, etc; a bridge or crown framework; or other prosthesis or portion of a prosthesis. In some embodiments, a full-anatomic prosthesis may be one in which the resulting prosthesis is ready for installation or implantation into a patient's mouth without further materials or components being added. A full-anatomic prosthesis may also be a prosthesis that has the final shape of the prosthesis, but will later be painted, dyed, or otherwise have its color modified before placement in a patient's mouth. In preparation for making or modifying a dental plan, an operator may load in models of the existing teeth, gums, and/or a wax-up of a prosthesis or abutment that is to be refined and then optionally upload a library of teeth as guidance for building the prosthesis.

Connectors between neighboring dental restoration component, such as pontics, crowns, prosthetic teeth, etc., in a full anatomic prosthesis, framework, etc. may be used to support these structures in the prosthesis and provide structural stability for the prosthesis. In a system that does not provide connector design, an operator may have to define the connectors between the dental restoration components by manipulating the surface of neighboring dental restoration components. Problems with that are many. For example, it may be difficult to understand or determine whether the connector between the dental restoration components is of sufficient cross-sectional area. If the connector between the dental restoration components is not of sufficient cross-sectional area, then the dental restoration components or the connector may fracture or otherwise not withstand the forces to which the prosthesis is subjected. Herein are described methods, systems and computer-readable media for defining connectors, without necessarily having to manipulate the surfaces of the dental restoration components that the connectors span.

In some embodiments, connectors between neighboring dental restoration components, such as those in a full-anatomic prosthesis, may be provided. Initially, a connector may be determined automatically based on the location of the teeth, minimal cross-sectional area, and/or other factors. After an initial connector is provided, the operator may desire a more appealing aesthetic outcome, or may want to change the connector for other reasons. For example, it may be desirable for the connector to be of sufficient cross-sectional area to support the prosthesis, but also designed in such a way that it is not visible or is only slightly visible when the patient smiles. As such, the user or operator may want to manipulate the connector or the connectors in order to change the appearance or other characteristic of the connector. The connector, once modified, will still have to meet any other acceptability design constraints on the connector.

Figure 9A:
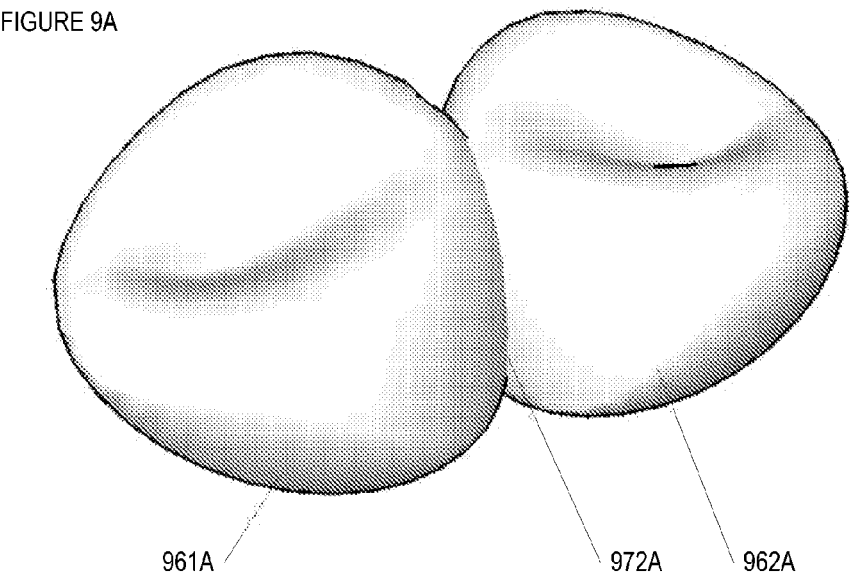
FIGS. 9A and 9B illustrate the intersection between two dental restoration components.
Figure 9B:
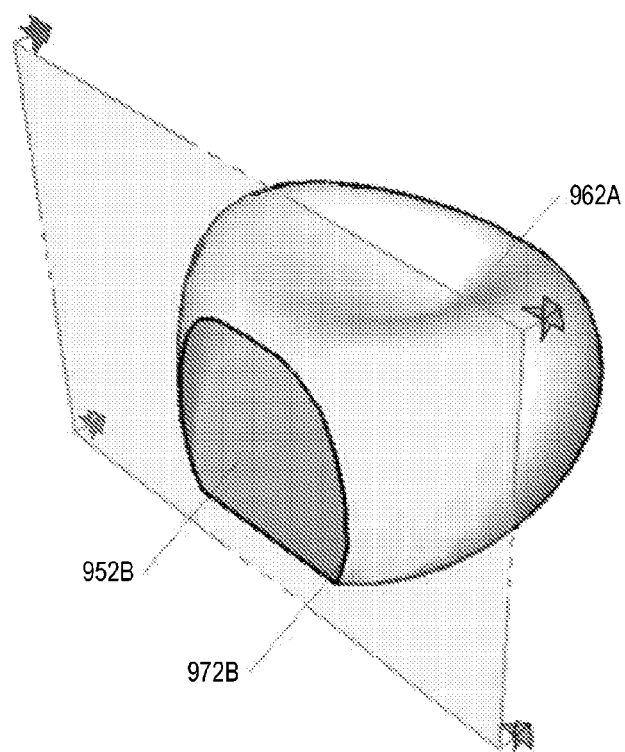

For example, it might not be possible to define a connector that excludes the intersection between two dental restoration components. FIGS. 9A and 9B illustrate the intersection between two dental restoration components. In FIG. 9A, the two dental restoration components 961A and 962A intersect along a curve 972A. As depicted in FIG. 9B, the curve 972B defines an area of overlap or intersection 952B between the dental restoration components. As described herein, this area of intersection 952B may be displayed to the operator in one or more portions of the display (describe in more detail herein).

For full anatomic restorations, for example, the spaces between dental restoration components (such as between a coping and a pontic) can be quite small. Therefore, it may be challenging to design a prosthesis that meets the acceptability design constraints, which are described more below, as well being aesthetically appealing. Similar challenges apply to frameworks and other prostheses. For example, in some embodiments, if the connector does meet an acceptability design constraint such as encompassing the area of intersection, then production of the dental prosthesis may improperly cut back the dental restoration components, thereby disturbing the dental plan. In some embodiments, if the connector does not include the area of intersection between two neighboring dental restoration components, then the overlapping area may still be included in the prosthetic plan, in which case more connective material may be used than specified in the plan. As another example of an acceptability design constraint, in some embodiments, there may be production constraints (such as millability) on the creation of connectors. For example, if the dental prosthesis is going to be milled, then there may be acceptability design constraints on the size and curvature of cavities that can be milled, and therefore, on the connector. A third example acceptability design constraint would be the cross-sectional area of the connectors, which may have a minimal value in order to provide sufficient support.

Generally, a connector will connect two dental restoration components, but the techniques herein apply whether there are two dental restoration components connected by a single connector or there are three or more dental restoration components connected by two or more connectors, and each of the connectors may be defined based on the techniques, systems, methods and computer-readable media described herein.

The techniques herein allow the user or operator to manipulate the connector and provide indications of whether the various acceptability design constraints on the connector are met. These indications and the various acceptability design constraints are described in more detail below.

Example Embodiment

FIG. 1 depicts an example computer-implemented interface for dental prosthesis connector design. The computer-implemented interface 100 may include an overlapped portion 110 and a connector cross-section portion 130. The interface may also include a localized abstraction portion 120, a global abstraction portion 121, as well as other portions, such as those depicted, such as a global visibility portion and various menus.

The connector between two dental restoration components may be visible, both in the overlapped portion 110 and the connector cross-section portion 130. For example, a connector is shown in the connector cross-section portion 130 having connection curves 150 and 151 defining the connector. In the overlapped portion 110, the connector is shown with two connection curves 141 and 140. The connection curves in the overlapped portion 110 and connector cross-section portion 130 may correspond to one another. For example, connection curve 140 may corresponds to connection curve 150, and connection curve 141 to connection curve 151. The interconnection between connection curves and connectors is described more below, e.g., with respect to FIG. 5. As shown in FIG. 1, connection curve 140 and connection curve 150 each have manipulable points on them that allow an operator to define where to and how to manipulate and move the connection curve. By manipulating the connection curve(s), the user or operator may be able to grow or shrink the connector, as well as move the connector.

A connection curve may be the interface or line between the connector and the neighboring dental restoration component, such as a pontic, tooth or implant supported crown, coping, etc. Therefore, when a connector is connecting two dental restoration components, it may have two connection curves—140 and 141 or 150 and 151. The overlapped portion may provide a rendered three-dimensional representation of the prosthesis from a particular viewpoint, and that viewpoint may be definable by the operator using various keyboard, mouse-click, or other interactions. The connector cross-section portion 130 may illustrate, e.g., in the distal or mesial direction, a representation of at least one of the dental restoration components, and various visual indications related to the connector and acceptable positions for the connector. The connector cross-section portion 130 may represent acceptability design constraints by, for example, showing an area representing the intersection between the two neighboring dental restoration components that the connector spans. This overlap area, or intersection area, shown in the connector cross-section portion 130, may be colored or patterned differently than the rest of the tooth in order to emphasize its importance, as well as to guide the user or operator in modifying the connector in order to define a connector that encompasses the intersection between the neighboring dental restoration components.

The connector cross-section portion 130 may also include shading, colors or patterns on particular areas in order to represent other acceptability design constraints, such as showing what areas are not acceptable based on manufacturing criteria. This is described more below. For example, if a milling tool is used, the radius or width of the milling tool may define what areas between the two dental restoration components are reachable, and therefore, where the connector should be. For example, if the production technique is milling and certain areas between the two dental restoration components cannot be milled away or otherwise extracted with the production technique used, then the connector should include those areas, and therefore, the connection curve should not pass through that area. By showing the shading, color, etc. on those areas that are not extractable, the operator will be able to manipulate the connection curves and thereby define the connector to include those areas that cannot be extracted.

Embodiments herein are not limited to the overlapped portion 110, localized abstraction portion 120, and connector cross-section portion 130. Various displays may include fewer than these three portions or may include other portions. For example, if there were a dental plan with three dental restoration components connected by two connectors, then there may be, for example, two connector cross-section portions 130, one for each of the two connectors. The portions of the display 100 may allow for more natural and intuitive connector design. Numerous other embodiments are described in detail herein.

Example System

Figure 2:
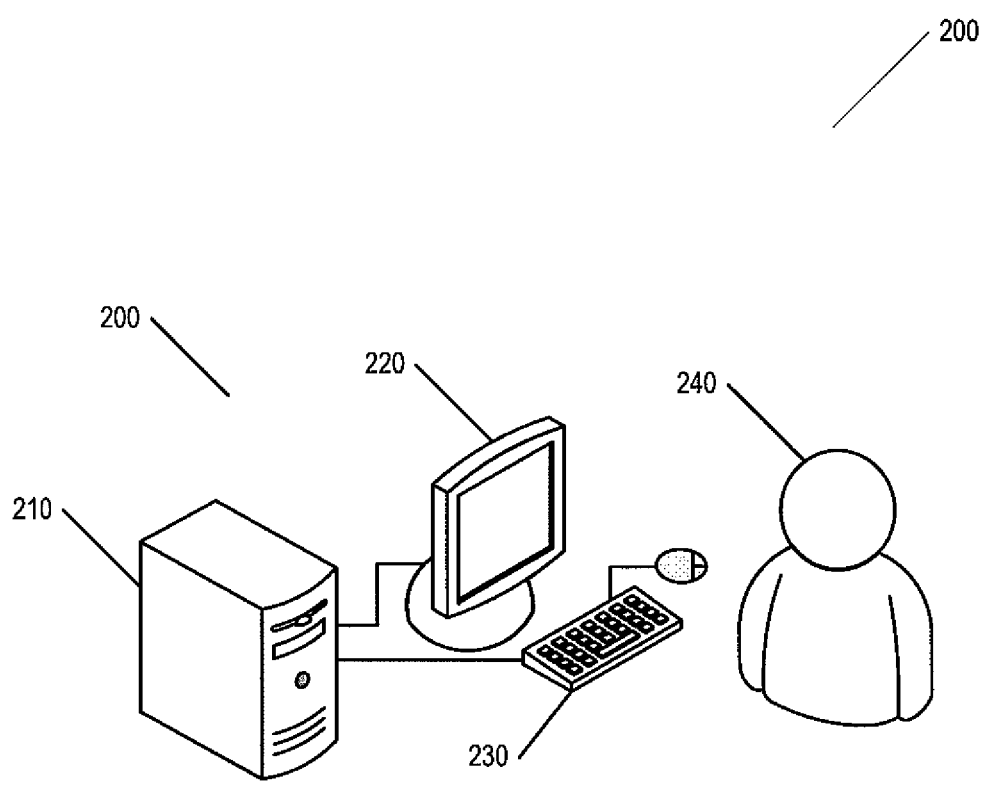
FIG. 2 illustrates an example system for dental prosthesis connector design.

FIG. 2 illustrates an example system 200 for dental prosthesis connector design. The system 200 may include one or more computers 210 coupled to one or more displays 220, and one or more input devices 230. An operator 240, who may be a dentist, dental technician, or other person, may plan dental prostheses using system 200 by manipulating the one or more input devices 230, which may be a keyboard and/or a mouse. In some embodiments, while working on the dental plan, the operator 240 may view the dental plan and other related dental data on the display 220. The display 220 may include two or more display regions or portions, each of which displays a different view of the dental data. For example, in some embodiments, the display 220 may show a semi-realistic 3D rendering of the dental data, a localized abstraction of the dental data, and/or a cross-sectional representation of the dental data. Each of these displays or portions may be linked internally within a program and/or using data on computer 210. For example, a program running on a computer 210 may have a single internal representation of the dental data in memory and the internal representation may be displayed in two or more abstract or semi-realistic manners on display 220.

In some embodiments, the operator 240 may be able to perform a command, such as select, move, manipulate, or make transparent, opaque, or invisible, on a particular substructure in the dental data. The operator 240 may be able to perform this command by manipulating the input device 230, such as clicking with a mouse on a particular region of one of the abstract or semi-realistic versions of the dental data displayed on the display 220. For example, an operator 240 may click the mouse on a connector for a tooth in order to select that connector. In some embodiments, if the operator selects a particular manipulable point on a connection curve of a connector, then the operator may be able to manipulate the position of the manipulable point by moving the mouse while holding down a mouse button, after selecting the manipulable point, etc.

In various embodiments, the computer 210 may include one or more processors, one or more memories, and one or more communication mechanisms. In some embodiments, more than one computer may be used to execute the modules, methods, and processes discussed herein. Additionally, the modules and processes herein may each run on one or multiple processors, on one or more computers; or the modules herein may run on dedicated hardware. The input devices 230 may include one or more keyboards (one-handed or two-handed), mice, touch screens, voice commands and associated hardware, gesture recognition, or any other means of providing communication between the operator 240 and the computer 210. The display 220 may be a two-dimensional ("2D") or 3D display and may be based on any technology, such as LCD, CRT, plasma, projection, etc.

The communication among the various components of system 200 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 200 may also be combined into a single unit or module. In some embodiments, all of the electronic components of system 200 are included in a single physical unit or module.

Process Overview

Figure 3:
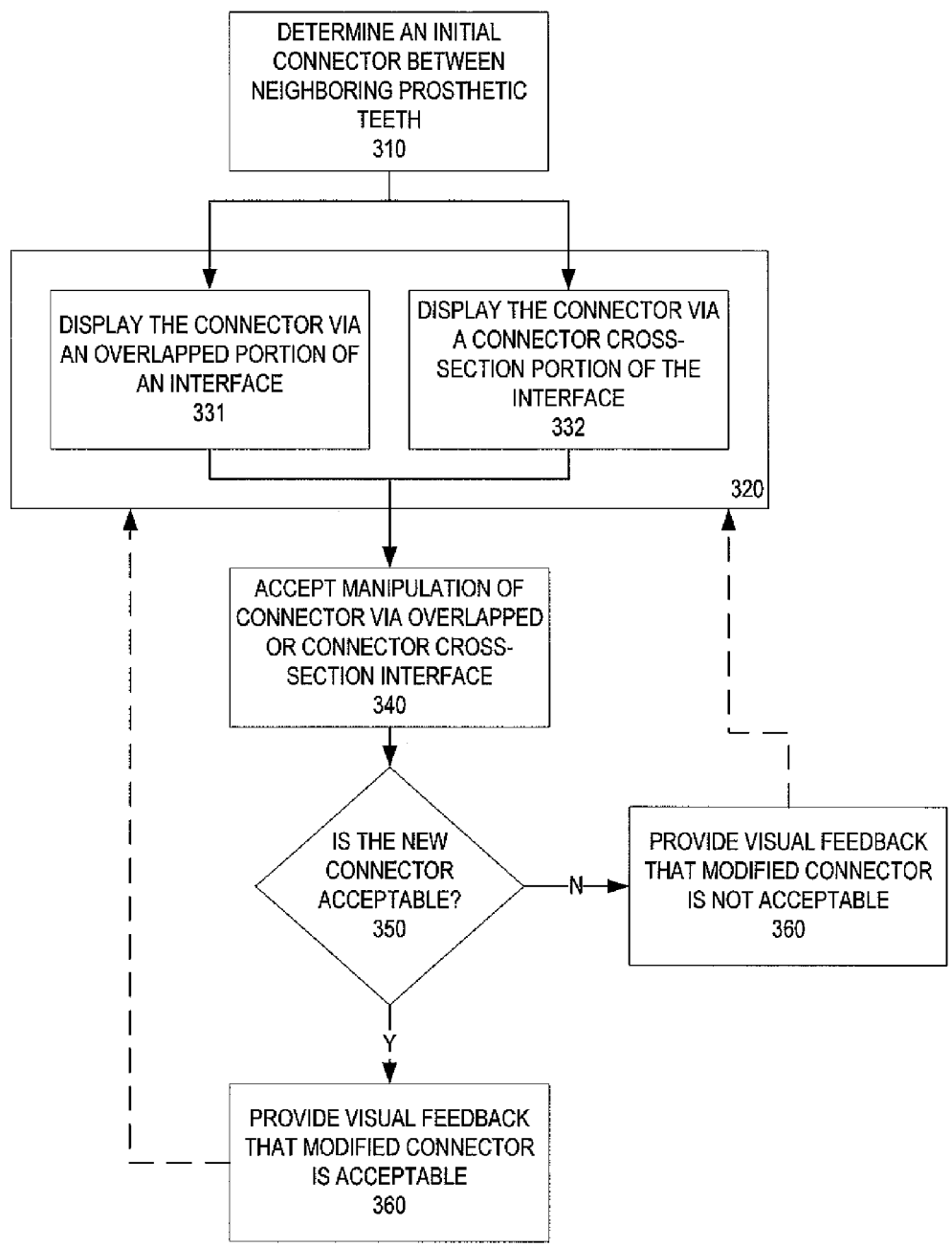
FIG. 3 illustrates a first method for dental prosthesis connector design.

FIG. 3 illustrates a method 300 for dental prosthesis connector design. In block 310, a first connector is determined for two or more neighboring dental restoration components. The neighboring dental restoration components may be part of a full anatomic prosthesis or prosthesis framework. If there are more than two dental restoration components in the prosthesis, then the method 300 may be performed for each set of two neighboring dental restoration components. Determining the connector between two neighboring dental restoration components may include determining a connector that encompasses any area of intersection between two neighboring dental restoration components. Further, in some embodiments, determining a connector between two neighboring dental restoration components may also include determining a connector that is of sufficient cross-sectional area. In some embodiments, the cross-sectional area necessary to support two neighboring dental restoration components may be determined based on the position of the two dental restoration components, the material used in the prosthesis, and/or any other appropriate factors.

After a connector between two dental restoration components is determined in block 310, then in block 320, the connector is displayed. The connector may be displayed in the overlapped portion in block 331 and/or in the connection cross-section portion in block 332. The overlapped portion of the computer-implemented interface may be similar to that depicted in FIG. 1 as portion 110. The overlapped portion of the computer-implemented interface may display the prosthesis in three dimensions with shading, rendered in a realistic or semi-realistic manner.

Displaying the connector in the overlapped portion of the interface in block 331 may also include displaying connection curves in the overlapped portion of the interface. A connection curve may represent the curve that defines the interface or border between the connector and a dental restoration component. As such, in some embodiments, there may be two connection curves for each connector. The connection curves may each correspond to a dental restoration component. For example, if the view from the lingual direction has a dental restoration components on the left and a dental restoration components on the right, and the connector is connecting those two dental restoration components, then there may be a connection curve between the connector and the left dental restoration components, as well as one between the connector and the right dental restoration components.

In some embodiments, one or both of the connection curves may have manipulation points thereon. The manipulation points may allow an operator to manipulate the position of the connection curve, thereby manipulating the connector with respect to the dental restoration components. For example, if a manipulation point is moved away from the center of the connector, then the connector may be expanded based on the new position of that manipulation point of the connector curve.

Figure 8:
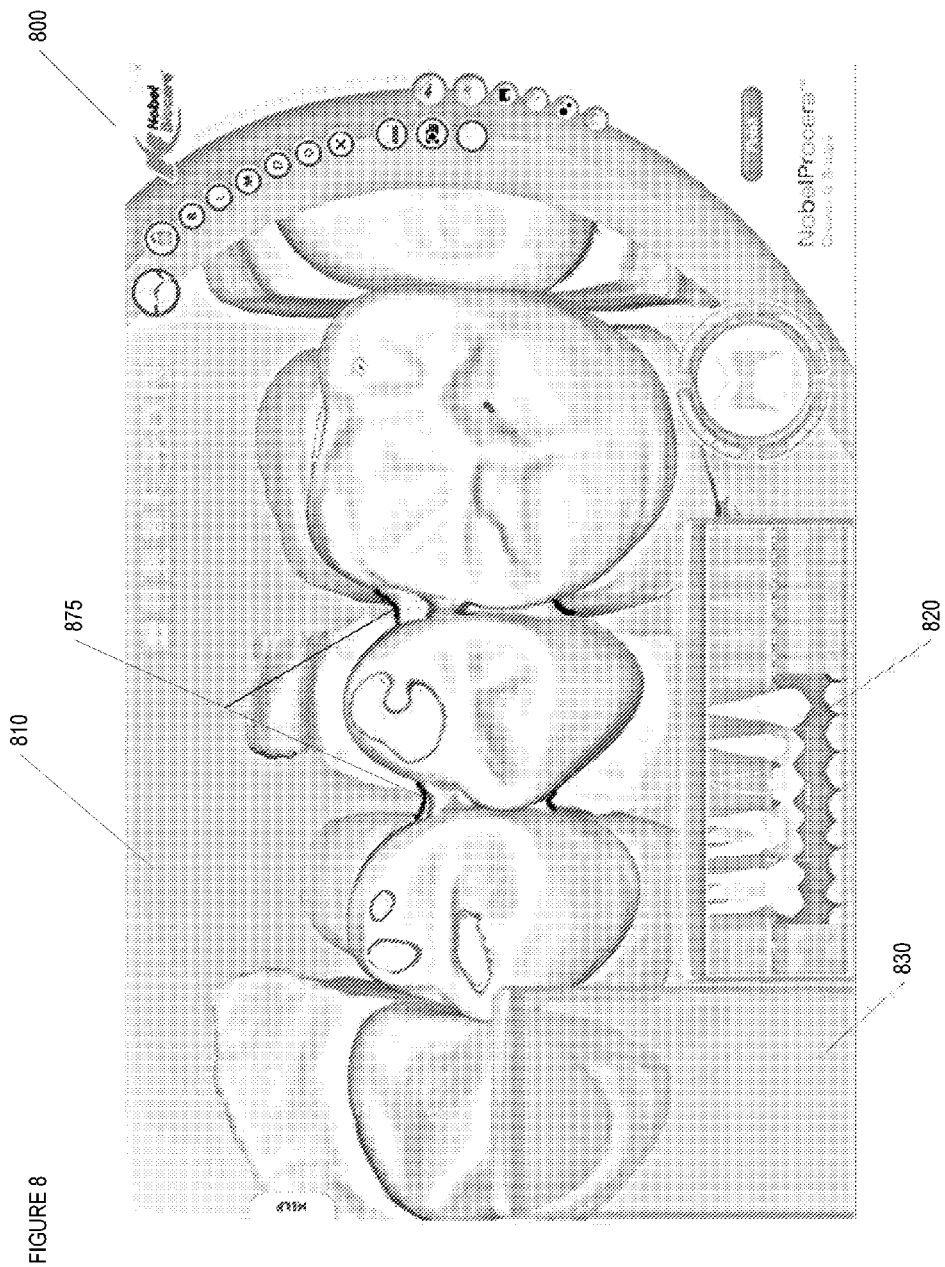
FIG. 8 illustrates a fifth display for dental prosthesis connector design.

In some embodiments, either simultaneously with block 331, before block 331, after block 331, or instead of performing block 331, the connector may also be displayed in a connector cross-section portion of the computer-implemented interface, as part of block 332. In some embodiments, the connector cross-section portion of the interface may not be shown unless it is pulled from a tab, clicked on in order to activate it, unless the connector is selected, or other appropriate measure. For example, as depicted in FIG. 8, in some embodiments, if the connector is not selected, then no connector may be shown in the connector cross-section portion 830 of the interface 800. In various embodiments, the connector cross-section portion of the interface may be on by default. That is, the connector cross-section portion of the interface may be viewable to the operator when the operator uses the computer-implemented interface, or the operator may have to activate the connector cross-section portion of the computer-implemented interface in order to see that portion.

The connector cross-section portion of the interface may display the distal or mesial view of a dental restoration component (as a rendered 3D object or other representation) as well as the connection curves for a connector connecting that restoration component to another dental restoration component. Displaying the connector via the connector cross-section portion of the interface may also include displaying manipulation points for one or both of the connection curves, such as manipulable points 581 for connection curve 550 in FIG. 5. The manipulation points on the connector cross-section portion may correspond to those shown on the overlapped portion. That is, in some embodiments, if one of the connection curves is manipulable in the overlapped portion of the interface, the same points or corresponding points may be manipulable in the connector cross-section portion. Displaying the connector in the connector cross-section portion of the interface may also include displaying one connection curve with manipulable points and another connection curve without manipulable points. These two connection curves may be the same color or different colors, patterns, widths, etc.

The choice of which connection curve to show with manipulable points may be made based on any appropriate heuristic. For example, in some embodiments, the connection curve that is further away, from the point of view of the camera or viewer, may be chosen as the curve for which manipulable points will be shown. If, in the overlapped portion, the orientation of the prosthesis is manipulated so that the tooth that had been further away from the camera or viewpoint is now closer to the camera or viewpoint, the other connection curve may be shown with manipulable points, and the connection curve that had been further away from the camera may no longer be shown with manipulable points. In other embodiments, other heuristics may be used to determine which connection curve to show with manipulable points. For example, in some embodiments, an operator using the computer implemented interface may be able to select which of the two connection curves are shown with manipulable points.

After displaying the connector in the overlapped portion of the interface and/or the connector cross-section portion of the interface in blocks 331 and 332, respectively, operator input may be accepted in order to manipulate the connection curve for the connector via the cross-sectional or overlapped portions of the interface, as part of block 340. As discussed elsewhere, the manipulation may include maneuvering or moving manipulable points on the connection curve. If two or more connection curves are manipulable, then the operator may be able to manipulate either or both of the connection curves, as part of block 340.

After one or both connection curves have been manipulated, a new connector may be determined based on the new positions of the connection curves. This step is not shown in FIG. 3. In some embodiments, a new connector is determined as the connection curves are moved. In some embodiments, a new connector is determined at predetermined intervals or after the connection curves have been moved or modified a predetermined number of times. Determining the new connector based on the new positions of the connector curve may be accomplished using the same algorithms and techniques discussed elsewhere herein. Generally, in some embodiments, if points on the connection curve are moved away from the center of the connector, then the connector will be expanded in that direction. If points on the connection curve are moved toward the center of the connector, then the connector may be made narrower in that direction.

After the connection curve has been manipulated as part of block 340, then in block 350 a check is made to determine whether the new connector is acceptable with respect to acceptability design constraints. Determining whether the new connector is acceptable with respect to acceptability design constraints may include numerous other determinations. For example, in some embodiments, the new connector may be checked against the intersection of the two dental restoration components that the connector is spanning. If the connector does not encompass the intersection between the two dental restoration components, then in some embodiments, a visual indication that the connector is not acceptable will be shown to the operator via the connector cross-section portion and/or the overlapped portion. For example, in some embodiments, if the connection curve is not in an acceptable position, then the operator may be able to see, in the connector cross-section portion of the interface, that the connection curve crosses over the intersection between the two dental restoration components. For example, in some embodiments, such as that depicted in FIG. 5, the intersection between two dental restoration components may be shown as a colored or patterned portion 552 in the connector cross-section portion 530. When the manipulable points 581 of a connection curve are moved and a new connection curve is defined, as described above, then the newly defined connection curve may be shown with respect to that intersection; that is, with respect to the colored or patterned portion representing the intersection 552. Since the connector must encompass the intersecting portion 552 of the two dental restoration components that the connector spans, showing that the connector is unacceptable may include showing that one of the connection curves 550 or 551 crosses through or intersects the area 552 shown as representing the intersection between the two dental restoration components. If the connector is unacceptable, then the connection curve 550 or 551 will be shown as intersecting the area of intersection 552 of the two dental restoration components (not depicted in FIG. 5).

In some embodiments, other indications of an unacceptable connector may be provided to the operator. These other visual indications may include flashing polygons or colors on the connector cross-section portion or overlapped portion, red or other colored outlines in the connector cross-section portion or overlapped portion, or may include audio feedback, such as a beep, sound, spoken phrase, or other indications that the connector is not in an acceptable position.

Block 350 may also include checking whether the connector is in a proper position with respect to production capabilities. For example, if the production technique is known, then it may be determined that the connector may not be formed or positioned in certain ways. For example, if a round-tipped milling technique is used, then in order to avoid cutting back neighboring dental restoration components, the connector may have to be defined so that its edges (the connection curves) are not in small crevices or spaces. If a connection curve's connection lines are in small crevices or spaces, then the connector may not be millable (e.g., the connection lines may not be reachable by the milling tool). That is, in some embodiments, the final shape of the connector should be millable without interfering with neighboring crowns or copings. As another example, if a large-tipped milling tool is used, then it will be impossible for the milling tool to fit between certain close portions of neighboring dental restoration components without cutting back those dental restoration components. If, however, a smaller milling tool is used, then the milling tool may be able to get closer into smaller spaces between the dental restoration components. Other production techniques will also have constraints. For example, an additive technique may have acceptability design constraints related to the manner and process for deposition of material.

If it is determined that the connector is improperly placed with respect to production constraints in block 350, then an indication of that incorrect position may be shown. The indications may be those described above, for example, that a visual overlap between the unacceptable production positions and the connection curve may be visible. As another example, if the connector is in an unacceptable position with respect to production constraints, another visual or audio feedback may be displayed or played for the operator. As a specific example, and looking again to FIG. 5, cross-hatched area 553 represents the area that a milling tool cannot reach. If the manipulable points 581 for connection curve 550 were manipulated such that the connection curve 550 were not acceptable (not depicted), then the operator may see that the connection curve 550 crosses over the unacceptable manufacturing position area 553.

In some embodiments, in block 350, a check is also made to determine whether the connector is of sufficient cross-sectional area for production. The required width of a connector may be, in some embodiments, defined based on the position of the pontics, crowns, or other structures that the connector spans. It may also be constrained based on the material being used, and other constraints. If the cross-sectional area is not sufficient, then a visual or audio indication, such as those described herein, may be shown to the operator. Further, in some embodiments, such as that depicted in FIG. 7, the display may include a portion 760 that includes text representing how much smaller the cross-sectional area is than the minimal requirement. For example, if the minimal cross-sectional area is 12 $mm^2$, and the cross-sectional area of the connector, as defined after manipulation, is 11.94 $mm^2$, then the operator may be see those numbers on a portion 760 of the display 700.

In some embodiments, if the cross-sectional area of the connector is smaller than the minimal cross-sectional area required, then the text for the cross-sectional area and/or the minimal cross-sectional area may be shown in different colors, as blinking text, in different fonts, in fonts of different sizes, or other indication to alert (including an audio alert) the operator to the fact that the cross-sectional area is not of sufficient width. As another example, and as depicted in FIG. 8, when the cross-sectional area is not sufficient, the operator may see a different color, width, or pattern of outline 875 of the connector in the overlapped portion 810 of display 800. In some embodiments, the connector may have a thick line 875, e.g., that outlines the connector in portion 810 in order to indicate to the operator that the connector is not of sufficient width. The line 875 may be thicker than other lines used in the display 800 in order to emphasize that the connector is not of sufficient cross-sectional area.

Other checks may also be performed on the connector. For example, a check may be made to determine whether the connector extends beyond the front or back of the dental restoration components, whether it is visible externally from the mouth, or other check. Additionally, one or more of the checks above may be performed together or apart, and in any order. In some embodiments, all of the checks described are performed, or a subset of the checks described is performed.

If, in block 350, it is determined that the new connector is acceptable, then, optionally, in block 370, feedback may be given to the operator indicating that the new connector, as defined by the manipulated connection curves, is acceptable. This indication may take any form, including an audio sound, a spoken phrase, visual feedback, such as showing in the connector cross-section portion that the connector does not overlap with the intersection portion and does not overlap with the unacceptable manufacturing positions, or any other feedback.

Figure 4:
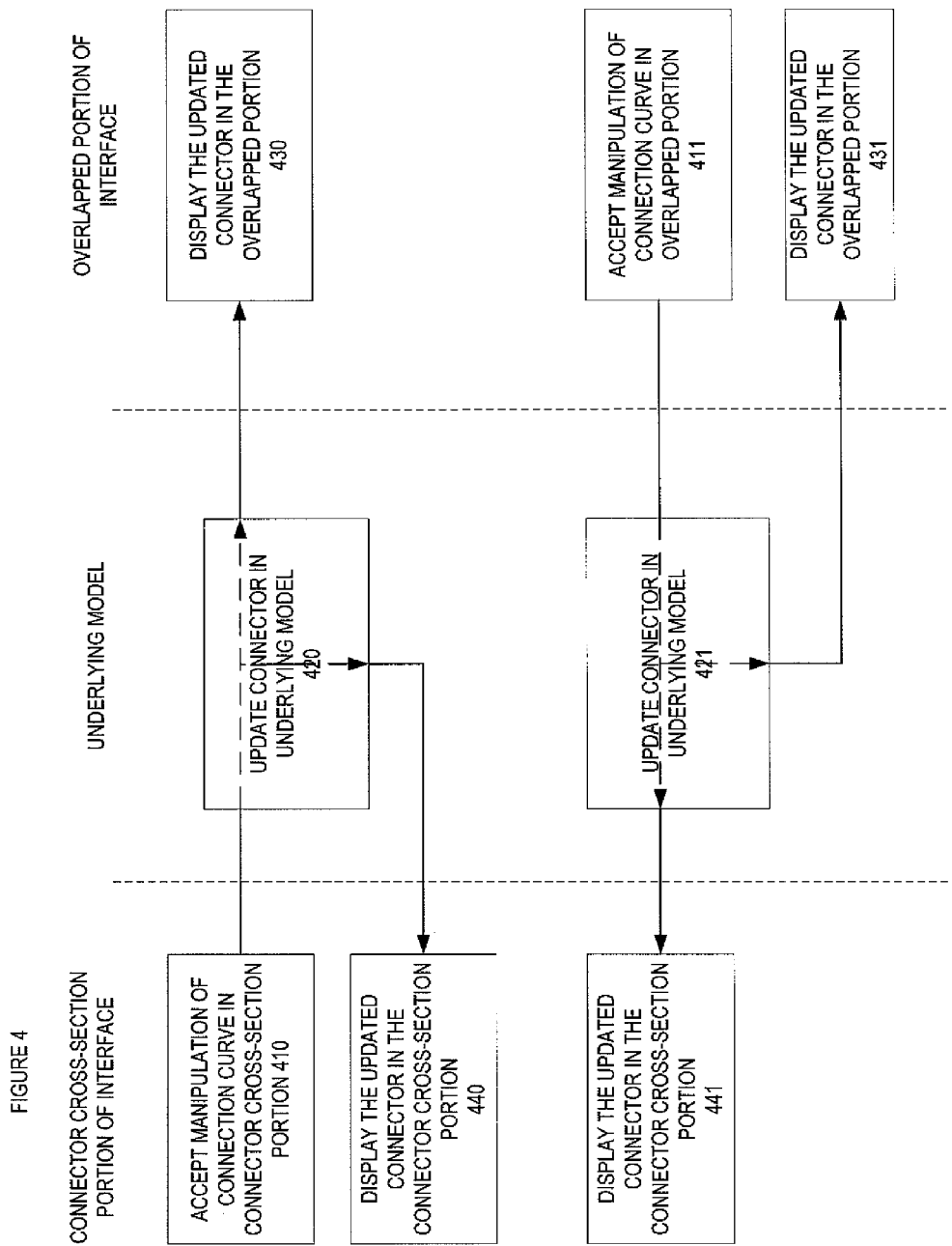
FIG. 4 illustrates a second method for dental prosthesis connector design.

FIG. 4 is a flow diagram depicting various connector manipulations and their effect on the connector cross-section portion of the interface, the overlapped portion of the interface, and the underlying model. Generally, in some embodiments, the connector cross-section portion of the interface and the overlapped portion of the interface may each be generated based on an underlying model of the dental restoration components and connector(s). Changes made by the operator in either the connector cross-section portion or overlapped portion of the interface may affect the underlying model and may be represented in the other portion of the interface. For example, consider FIG. 1. If a change is made to either connection curve 140 or 150, then an underlying model of the connector may be altered (e.g., using the method 300 of FIG. 3), and the change to the underlying model of the connector may be reflected in both the overlapped portion of the interface 110 and the connector cross-section portion of the interface 130. Returning again to FIG. 4, after accepting manipulation of a connection curve in the connector cross-section portion of the interface in block 410, an update corresponding to that manipulation may be made to the underlying model in block 420. After the connector is updated in the underlying model, then in blocks 430 and 440, the updated connector is displayed in the overlapped portion and connector cross-section portion, respectively.

The underlying model may be updated in any appropriate manner. For example, in some embodiments, the connector will have a waist or indentation between the two connection curves, that is, if looked at from the side, the highest point on each connection curve will have a curve running between them in which the connector gets skinnier towards the center. In some embodiments, the connector will be defined by straight lines between the two connection curves.

As also depicted in FIG. 4, the underlying model may be manipulated by performing manipulations of connection curves in the overlapped portion of the interface. For example, if, in block 411, manipulations are accepted in the overlapped portion of the computer-implemented interface, then in block 421, an update is made to the connector in the underlying model. Each time an update is made to the underlying model, in some embodiments, the update to the connector is reflected in the connector cross-section portion of the interface in block 441, and the overlapped portion of the interface in block 431.

Additional Embodiments

Embodiments related to FIGS. 5 through 8 are discussed throughout and additional embodiments are discussed below.

Figure 5:
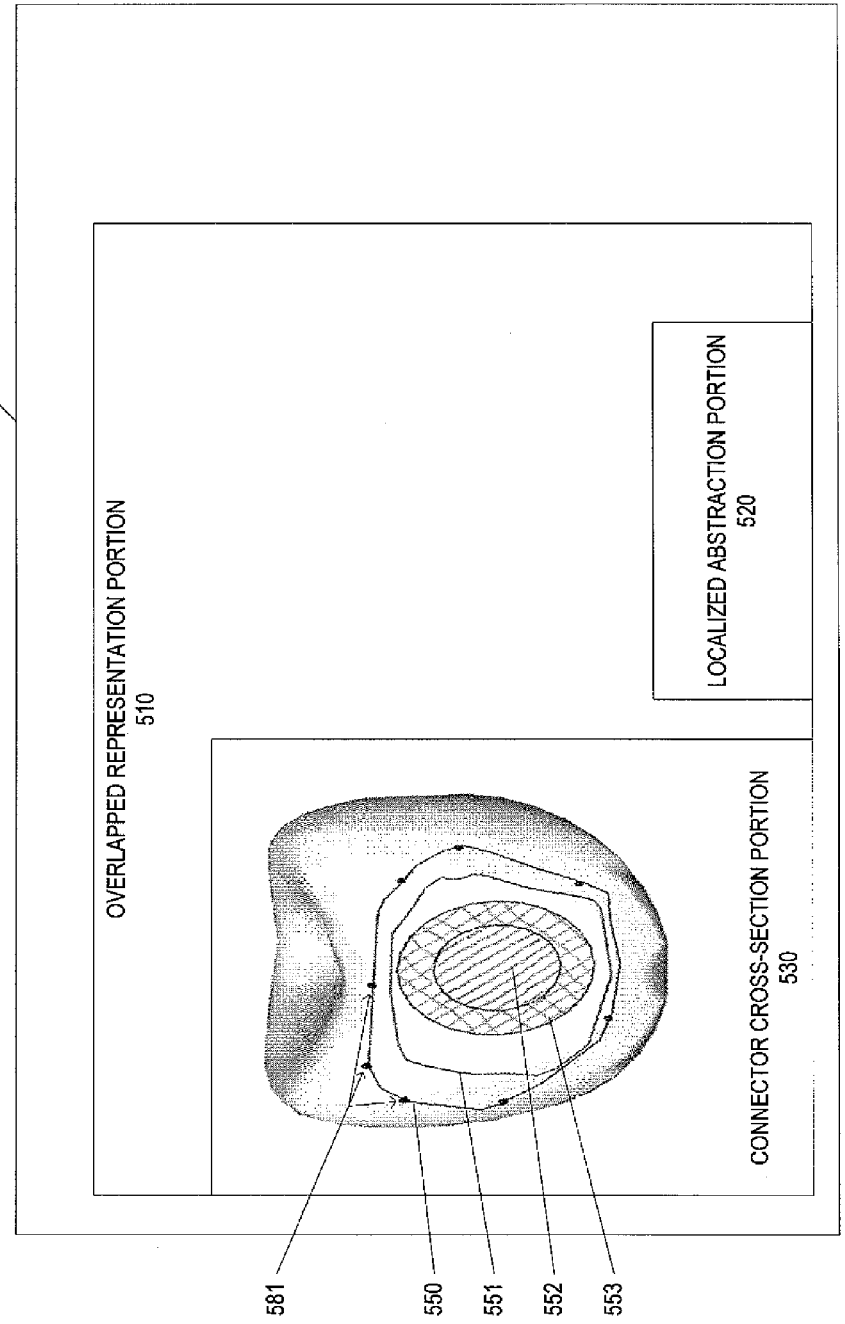
FIG. 5 illustrates a second display for dental prosthesis connector design.

FIG. 5 illustrates a second display 500 for dental prosthesis connector design. FIG. 5 is described above and additionally depicts that the relative proportions of the portions 510, 520, and 530 of display 500 may vary from those depicted in other figures. Further, portions 510, 520, and 530 may be in other locations and may have other proportions than those depicted herein.

Figure 6:
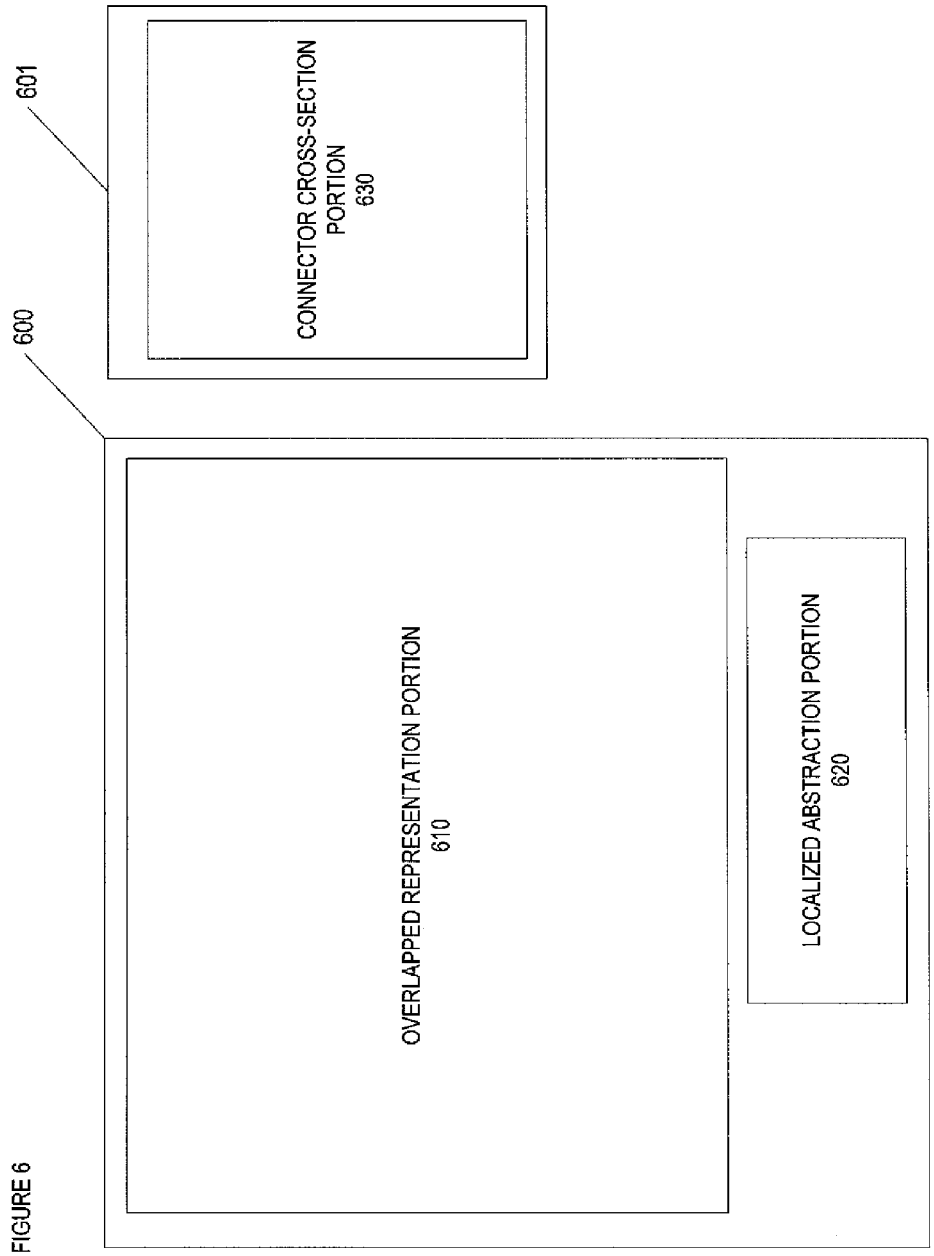
FIG. 6 illustrates a third display for dental prosthesis connector design.

FIG. 6 illustrates a third set of displays 600 and 601 for dental prosthesis connector design. As illustrated in FIG. 6, one or more of portions 610, 620, and 630 may be shown on a separate display from the others. In FIG. 6, the connector cross-section portion 630 is shown on display 601 and the overlapped portion 610 and the localized abstraction portion 620 are shown on a different display 601. The two displays 600 and 601 on which the portions 610, 620, and 630 are shown may be separate physical display, separate windows on a single display or any other appropriate separation. Further, in some embodiments, the portions may be displayed on more than two displays or each portion may be shown on its own display. Additionally, in some embodiments fewer or more portions of the interface may be shown, such as the cross-sectional area portion 760 shown in FIG. 7.

Figure 7:
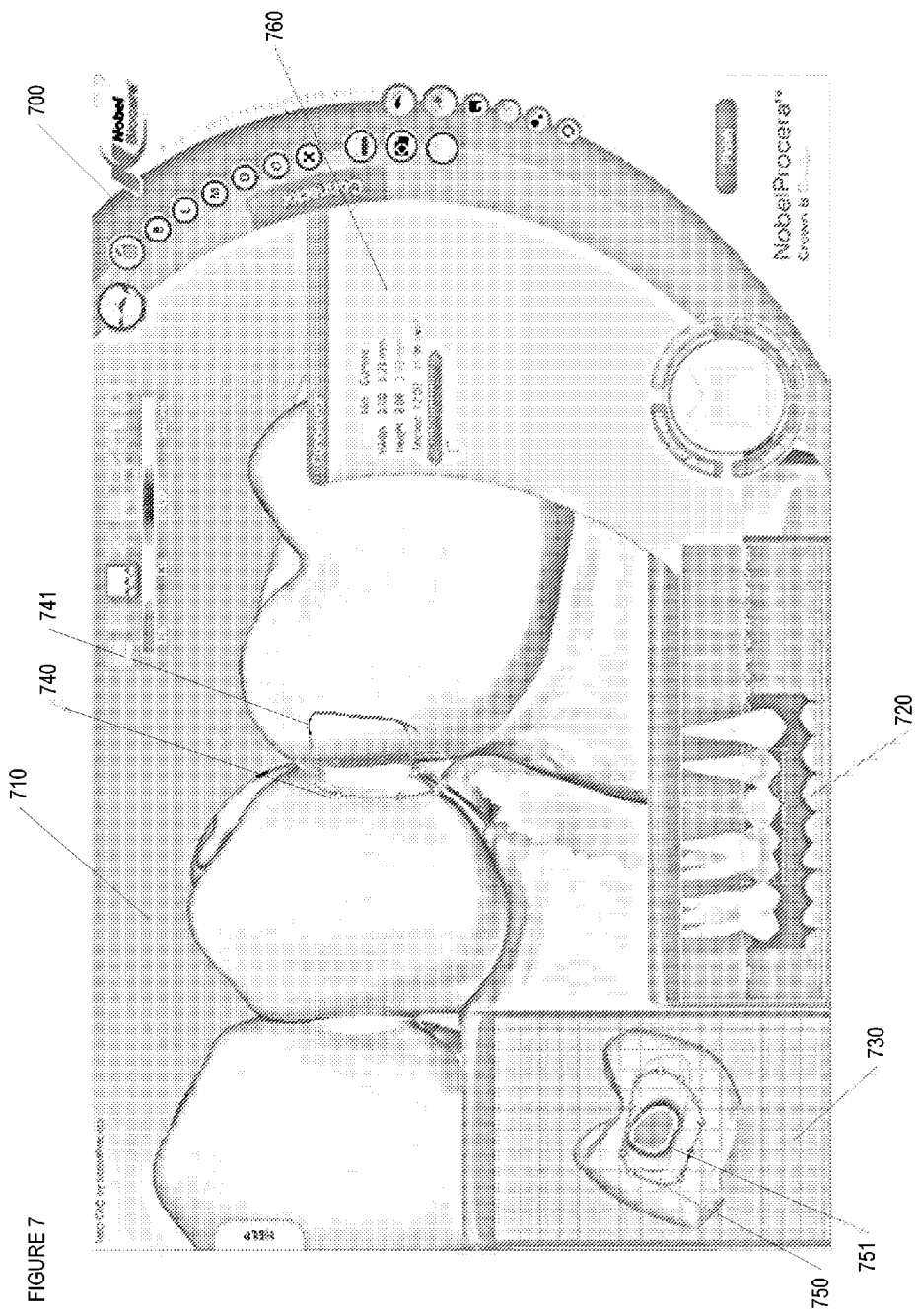
FIG. 7 illustrates a fourth display for dental prosthesis connector design.

FIG. 7 illustrates a fourth display 700 for dental prosthesis connector design. As depicted in FIG. 7, information about minimal and current cross-sectional area may be shown in cross-sectional area portion 760. FIG. 7 also illustrates that when a connector is selected in the localized abstraction portion 720 or the overlapped portion 710, that connector may be shown in the connector cross-section portion 730.

FIG. 8 illustrates a fifth display 800 for dental prosthesis connector design. As depicted in FIG. 8, when no connector is selected, the connector may not appear in the connector cross-section portion 830.

The processes and systems described herein may be performed on or encompass various types of hardware, such as computer systems. In some embodiments, computer 210, display 220, and/or input device 230 may each be separate computer systems, applications, or processes or may run as part of the same computer systems, applications, or processes—or one or more may be combined to run as part of one application or process—and/or each or one or more may be part of or run on a computer system. A computer system may include a bus or other communication mechanism for communicating information, and a processor coupled with the bus for processing information. The computer systems may have a main memory, such as a random access memory or other dynamic storage device, coupled to the bus. The main memory may be used to store instructions and temporary variables. The computer systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys. Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also include messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions, blocks, or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A computer-implemented method for design of a connector between a first dental restoration component and a second dental restoration component of a dental prosthesis, comprising:
   displaying, from a cross-sectional viewpoint, in a first frame of a computer-based interface,
      the first dental restoration component representing a crown, a coping, a pontic, or a prosthetic tooth,
      a first connection curve representing an interface between the connector and the first dental restoration component, the first connection curve comprising first manipulable points configured to allow an operator to change the size and/or position of the first connection curve,
      a second connection curve representing a second interface between the connector and the second dental restoration component, and
      an area proximal and visually distinguishable from the first dental restoration component representing a region satisfying an acceptability design constraint for the connector;
   displaying, from a user selected viewpoint different from the cross-sectional viewpoint and rendered in three dimensions, in a second frame of the computer-based interface distinct from the first frame,
      the first dental restoration component,
      the second dental restoration component representing a crown, a coping, a pontic, or a prosthetic tooth, and
      a third connection curve, corresponding to the first connection curve, representing the interface between the connector and the first dental restoration component, the third connection curve comprising second manipulable points configured to allow the operator to change the size and/or position of the third connection curve;
   receiving a modification based on operator input representing a manipulation by the operator of the first connection curve in the first frame or the third connection curve in the second frame;
   determining whether the modification is acceptable with respect to the acceptability design constraint; and
   providing a visual indication to the operator via both the first frame and the second frame based at least in part on whether the modification is acceptable with respect to the acceptability design constraint, the visual indication providing an indication that the first connection curve or the third connection curve overlaps an unacceptable production area,
   the method performed programmatically by a computer-aided design system that comprises one or more physical computers.

2. The method of claim 1, wherein the prosthesis is a full anatomic restoration.

3. The method of claim 1, wherein the method further comprises: providing, via the first frame, a second indication of where the first dental restoration component and the second dental restoration component intersect.

4. The method of claim 1, wherein determining whether the modification is acceptable comprises determining whether the modification is acceptable relative to an intersection of the first dental restoration component and the second dental restoration component.

5. The method of claim 1, wherein the area comprises a colored region in the cross-sectional representation.

6. The method of claim 1, wherein the area comprises a patterned region.

7. The method of claim 1, wherein the second connection curve is non-manipulable.

8. The method of claim 1, wherein the method further comprises providing, via the computer-based interface, an acceptability indication of whether the connector is of sufficient cross-sectional area to meet material constraints.

9. The method of claim 1, wherein the method further comprises:
   determining whether the connector with the modification is of sufficient cross-sectional area; and
   in response to determining that the connector with the modification is not of sufficient cross-sectional area, providing an acceptability indication via the computer-based interface that the connector with the modification is not of sufficient cross-sectional area.

10. The method of claim 9, wherein providing the acceptability indication comprises providing a colored border for the connector with the modification in the second frame.

11. The method of claim 9, wherein providing the acceptability indication comprises providing a textual representation that the connector with the modification is not of sufficient cross-sectional area.

12. The method of claim 1, wherein the method further comprises automatically determining an initial position of the connector, prior to the modification, based at least in part on the first dental restoration component and the second dental restoration component.

13. The method of claim 1, wherein the method further comprises producing a physical version of the prosthesis comprising the first dental restoration component, the second dental restoration component, and the connector with the modification.

14. The method of claim 1, wherein the first dental restoration component is a pontic.

15. A system for design of a connector between a first dental restoration component and a second dental restoration component of a dental prosthesis, said system comprising:
   a computer system comprising computer hardware, the computer system programmed to:
   display, from a cross-sectional viewpoint, in a first frame of a computer-based interface, the first dental restoration component representing a crown, a coping, a pontic, or a prosthetic tooth, a first connection curve representing an interface between the connector and the first dental restoration component, the first connection curve comprising first manipulable points configured to allow an operator to change the size and/or position of the first connection curve, a second connection curve representing a second interface between the connector and the second dental restoration component, and an area proximal and visually distinguishable from the first dental restoration component representing a region satisfying an acceptability design constraint for the connector;

display, from a user selected viewpoint different from the cross-sectional viewpoint and rendered in three dimensions, in a second frame of the computer-based interface distinct from the first frame, the first dental restoration component, the second dental restoration component representing a crown, a coping, a pontic, or a prosthetic tooth, and a third connection curve, corresponding to the first connection curve, representing the interface between the connector and the first dental restoration component, the third connection curve comprising second manipulable points configured to allow the operator to change the size and/or position of the third connection curve;

receive a modification based on operator input representing a manipulation by the operator of the first connection curve in the first frame or the third connection curve in the second frame;

determine whether the modification is acceptable with respect to the acceptability design constraint, the determination comprising determining whether the modification is acceptable relative to an intersection of the first dental restoration component and the second dental restoration component; and provide a visual indication to the operator via both the first frame and the second frame based at least in part on whether the modification is acceptable with respect to the acceptability design constraint.

16. The system of claim 15, wherein the visual indication comprises an indication that the first connection curve or the third connection curve overlaps an unacceptable production area.

17. A computer-readable non-transitory storage medium comprising computer-executable instructions for performing a method for design of a connector between a first dental restoration component and a second dental restoration component of a dental prosthesis, the method comprising:

displaying, from a cross-sectional viewpoint, in a first frame of a computer-based interface, the first dental restoration component representing a crown, a coping, a pontic, or a prosthetic tooth, a first connection curve representing an interface between the connector and the first dental restoration component, the first connection curve comprising first manipulable points configured to allow an operator to change the size and/or position of the first connection curve, a second connection curve representing a second interface between the connector and the second dental restoration component, and an area proximal and visually distinguishable from the first dental restoration component representing a region satisfying an acceptability design constraint for the connector;

displaying, from a user selected viewpoint different from the cross-sectional viewpoint and rendered in three dimensions, in a second frame of the computer-based interface distinct from the first frame, the first dental restoration component, the second dental restoration component representing a crown, a coping, a pontic, or a prosthetic tooth, and a third connection curve, corresponding to the first connection curve, representing the interface between the connector and the first dental restoration component, the third connection curve comprising second manipulable points configured to allow the operator to change the size and/or position of the third connection curve;

receiving a modification based on operator input representing a manipulation by the operator of the first connection curve in the first frame or the third connection curve in the second frame;

determining whether the modification is acceptable with respect to the acceptability design constraint; and providing to the operator via both the first frame and the second frame a visual indication based at least in part on whether the modification is acceptable with respect to the acceptability design constraint and an acceptability indication of whether the connector is of sufficient cross-sectional area to meet material constraints.

18. The computer-readable storage medium of claim 17, wherein providing an acceptability indication comprises providing an indication that the first connection curve or the third connection curve overlaps an unacceptable production area.

19. The computer-readable storage medium of claim 17, wherein determining whether the modification is acceptable comprises determining whether the modification is acceptable relative to an intersection of the first dental restoration component and the second dental restoration component.

* * * * *